(12) United States Patent
Webber et al.

(10) Patent No.: US 12,324,721 B2
(45) Date of Patent: Jun. 10, 2025

(54) DENTAL ATTACHMENT POSITIONING APPARATUSES

(71) Applicant: Align Technology, Inc., San Jose, CA (US)

(72) Inventors: Peter Webber, Redwood City, CA (US); Yan Chen, Cupertino, CA (US); Jihua Cheng, San Jose, CA (US); Bastien Pesenti, San Jose, CA (US); Chunhua Li, Cupertino, CA (US); Jennifer C. Chen, San Francisco, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 18/435,971

(22) Filed: Feb. 7, 2024

(65) Prior Publication Data
US 2024/0173102 A1    May 30, 2024

Related U.S. Application Data (63) Continuation of application No. 14/939,252, filed on Nov. 12, 2015, now Pat. No. 11,931,222.

(51) Int. Cl.
*A61C 7/08*    (2006.01)
*A61B 1/00*    (2006.01)
(Continued)

(52) U.S. Cl.
CPC .............. *A61C 7/08* (2013.01); *A61B 1/0002* (2013.01); *A61B 1/00045* (2013.01); *A61B 1/24* (2013.01);
(Continued)

(58) Field of Classification Search
CPC ......... A61C 19/003; A61C 19/00; A61C 7/08; A61C 7/146; A61C 7/16; A61C 7/14;
(Continued)

(56) References Cited

U.S. PATENT DOCUMENTS 5,820,368 A    10/1998   Wolk
6,386,864 B1    5/2002   Kuo
(Continued)

FOREIGN PATENT DOCUMENTS

WO    WO-2009075977 A1 *  6/2009  ............. A61C 19/02

OTHER PUBLICATIONS

Alauddin et al., Positive distortion correcting device and method for manufacturing and using the positive distortion correcting for the device, CN 105517504 A, Machine translation (Year: 2016).*

*Primary Examiner* — Ralph A Lewis
*Assistant Examiner* — Mirayda A Aponte
(74) *Attorney, Agent, or Firm* — Shay Glenn LLP (57) ABSTRACT

Dental attachment positioning apparatuses and methods of use. A dental attachment apparatus may include an orthodontic attachment having a surface shaped to conform to a contour of a buccal surface of a tooth, and one or more registration surfaces that are shaped to conform to one or more occlusal surfaces of the patient's teeth. The one or more registration surfaces may be configured to aid in proper positioning or orientation of the orthodontic attachment. When the attachment positioning apparatus is placed on the patient's dentition, the orthodontic attachment is positioned at a specified location with respect to the buccal surface of the tooth.

20 Claims, 5 Drawing Sheets

(51) Int. Cl.
*A61B 1/24* (2006.01)
*A61C 7/14* (2006.01)
*A61C 7/16* (2006.01)
*A61C 13/15* (2006.01)
*A61N 5/06* (2006.01)

(52) U.S. Cl.
CPC ............... *A61C 7/146* (2013.01); *A61C 7/16* (2013.01); *A61C 19/003* (2013.01); *A61C 2202/01* (2013.01); *A61N 2005/063* (2013.01); *A61N 2005/0661* (2013.01)

(58) Field of Classification Search
CPC ........... A61C 7/12; A61C 7/00; A61C 7/0002; A61C 2202/01; A61B 1/0002; A61B 1/00039; A61B 1/00045; A61B 1/24; A61B 1/00043; A61N 2005/063; A61N 2005/0661; A61N 2005/0658; A61N 5/06; B33Y 80/00; B33Y 10/00; B33Y 30/00; B33Y 50/00; B33Y 70/00; B29L 2009/00
USPC ....................................................... 433/6, 29
See application file for complete search history.

(56) References Cited

U.S. PATENT DOCUMENTS

| | | |
|---|---|---|
| 6,783,604 B2 | 8/2004 | Tricca |
| 6,790,035 B2 | 9/2004 | Tricca et al. |
| 6,947,038 B1 | 9/2005 | Anh et al. |
| 7,104,792 B2 | 9/2006 | Taub et al. |
| 7,160,107 B2 | 1/2007 | Kopelman et al. |
| 7,448,514 B2 | 11/2008 | Wen |
| 7,600,999 B2 | 10/2009 | Knopp |
| 7,766,658 B2 | 8/2010 | Tricca et al. |
| 7,771,195 B2 | 8/2010 | Knopp et al. |
| 7,871,269 B2 | 1/2011 | Wu et al. |
| 7,883,334 B2 | 2/2011 | Li et al. |
| 7,914,283 B2 | 3/2011 | Kuo |
| 8,235,715 B2 | 8/2012 | Kuo |
| 8,337,199 B2 | 12/2012 | Wen |
| 8,401,686 B2 | 3/2013 | Moss et al. |
| 8,562,337 B2 | 10/2013 | Kuo et al. |
| 8,684,729 B2 | 4/2014 | Wen |
| 8,758,009 B2 | 6/2014 | Chen et al. |
| 9,119,691 B2 | 9/2015 | Namiranian et al. |
| 9,326,831 B2 | 5/2016 | Cheang |
| 9,655,691 B2 | 5/2017 | Li et al. |
| 9,700,385 B2 | 7/2017 | Webber |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,363,116 B2 | 7/2019 | Boronkay |
| D865,180 S | 10/2019 | Bauer et al. |
| 10,463,452 B2 | 11/2019 | Matov et al. |
| 10,492,888 B2 | 12/2019 | Chen et al. |
| 10,517,701 B2 | 12/2019 | Boronkay |
| 10,537,463 B2 | 1/2020 | Kopelman |
| 10,555,792 B2 | 2/2020 | Kopelman et al. |
| 10,588,776 B2 | 3/2020 | Cam et al. |
| 10,743,964 B2 | 8/2020 | Wu et al. |
| 10,781,274 B2 | 9/2020 | Liska et al. |
| 10,881,487 B2 | 1/2021 | Cam et al. |
| 10,912,629 B2 | 2/2021 | Tanugula et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 11,259,896 B2 | 3/2022 | Matov et al. |
| 11,278,375 B2 | 3/2022 | Wang et al. |
| 11,318,667 B2 | 5/2022 | Mojdeh et al. |
| 11,331,166 B2 | 5/2022 | Morton et al. |
| 11,419,710 B2 | 8/2022 | Mason et al. |
| 11,471,253 B2 | 10/2022 | Venkatasanthanam et al. |
| 11,497,586 B2 | 11/2022 | Kopelman |
| 11,504,214 B2 | 11/2022 | Wu et al. |
| 11,523,881 B2 | 12/2022 | Wang et al. |
| 11,564,777 B2 | 1/2023 | Kopelman et al. |
| 11,571,278 B2 | 2/2023 | Kopelman et al. |
| 11,571,279 B2 | 2/2023 | Wang et al. |
| 11,576,752 B2 | 2/2023 | Morton et al. |
| 11,589,955 B2 | 2/2023 | Medvinskaya et al. |
| 11,602,414 B2 | 3/2023 | Sato et al. |
| 11,642,194 B2 | 5/2023 | Boronkay et al. |
| 11,642,198 B2 | 5/2023 | Kopelman et al. |
| 11,666,415 B2 | 6/2023 | Wang et al. |
| 11,701,203 B2 | 7/2023 | Makarenkova et al. |
| 11,737,857 B2 | 8/2023 | Derakhshan et al. |
| 11,779,243 B2 | 10/2023 | Li et al. |
| 11,779,437 B2 | 10/2023 | Cam et al. |
| 11,793,606 B2 | 10/2023 | Cam et al. |
| 11,931,222 B2 | 3/2024 | Webber et al. |
| 11,931,223 B2 | 3/2024 | Shanjani et al. |
| 11,937,991 B2 | 3/2024 | Webber et al. |
| 2004/0166462 A1 | 8/2004 | Phan et al. |
| 2005/0014105 A1 | 1/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0199142 A1 | 9/2006 | Liu et al. |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2014/0067334 A1 | 3/2014 | Kuo |
| 2016/0193014 A1 | 7/2016 | Morton et al. |
| 2017/0007359 A1 | 1/2017 | Kopelman et al. |
| 2020/0155276 A1 | 5/2020 | Cam et al. |
| 2020/0188062 A1 | 6/2020 | Kopelman et al. |
| 2021/0147672 A1 | 5/2021 | Cole et al. |

\* cited by examiner

DENTAL ATTACHMENT POSITIONING APPARATUSES

CLAIM OF PRIORITY

This application is a continuation of U.S. patent application Ser. No. 14/939,252, titled "DENTAL ATTACHMENT FORMATION STRUCTURES," filed Nov. 12, 2015, now U.S. Patent Application Publication No. 2017/0135793, which is herein incorporated by reference in its entirety.

BACKGROUND

The present disclosure provides methods, computing device readable medium, devices, and systems that utilize dental attachment formation structures during dental treatment. Dental treatments involve restorative and/or orthodontic procedures to improve the quality of life of a patient.

For example, restorative procedures may be designed to implant a dental prosthesis (e.g., a crown, bridge, inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth or a jaw of a patient over a period of time.

As an example, orthodontic repositioning may be provided through a dental process that uses positioning appliances for realigning teeth. Such appliances may utilize a shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement. Appliances can also be used for other dental conditions, such as application of medications, appliances to help with sleep apnea, and other issues.

Attachments are affixed to the one or more teeth of the patient (typically with an adhesive material, such as an attachment composite material) or directly cured to a tooth. These attachments interact with surfaces on the appliance to impart forces on one or more teeth.

Such systems typically utilize a set of appliances that can be used serially such that, as the teeth move, a new appliance from the set can be implemented to further move the teeth without having to take a new impression of the patient's teeth at every increment of tooth movement in order to make each successive appliance. The same attachments may be utilized or attachments may be added, removed, or replaced with other attachment shapes that may impart different force characteristics than a previous appliance and attachment combination (i.e., appliance and one or more attachments).

Currently, attachments may be formed by hand by a treatment professional (e.g., a doctor or assistant). In some implementations, a treatment professional selects an attachment material to be used and mixes ingredients to create the material, in a well, formed in a sheet of material, to the desired exterior shape of the attachment is provided to the treatment professional and the mixed attachment material is pushed into the well to form the attachment based on the shape of the well. The attachment is then removed from the well and then put on a tooth and cured.

However, treatment professionals can make one or more errors when mixing, forming, positioning, orienting, or securing one or more of the attachments and as such, the appliance and attachment combination may not fit together correctly or impart the correct one or more forces. The mixing of the attachment material and amount of attachment composite put into attachment wells on templates are uncontrolled, and therefore errors can occur. The absolute position of the attachment on the tooth is also subject to user error. In order to cure the material, a hand held ultraviolet light (UV light) is then inserted into the mouth of the patient in order to cure the attachments and placement of the light relative to the attachment is subject to error.

SUMMARY OF THE DISCLOSURE

Described herein are methods, devices and systems related to dental attachment formation structures. The dental attachment formation structures may be configured to form, position, orient and/or secure one or more orthodontic attachments to a patient's tooth or teeth.

According to one embodiment, a dental appliance comprises: a body having a first surface shaped to abut an exterior surface of a tooth and a well portion of the first surface shaped to form an attachment that is to be attached to the exterior surface of the tooth; a release layer formed over a surface of the well to allow the attachment to be removed from the well; and an attachment material that is used to form the attachment positioned within the well. The well may have a first opening to allow the attachment material to be placed in contact with the exterior surface of the tooth. The appliance may include a release liner formed over the attachment material to retain the attachment material within the well portion and then the release liner being removed prior to attaching the attachment to the exterior surface of the tooth. The well portion of the first surface may include a second opening that allows for the attachment material to be placed within the well while the release liner is positioned over the first opening. The appliance may further include a light curable adhesive material on a surface of the attachment for attaching the attachment to the tooth. The adhesive material may be an attachment composite material. At least a portion of the body may be made of a light transmissive material to allow light from the light source to cure a light curable material in contact with the tooth. At least a portion of the body may be made of a transparent material that is transparent to visible light.

According to another embodiment, a dental appliance comprises: a body having a first surface shaped to abut an exterior surface of a tooth; and a well portion of the first surface shaped to form a well to accommodate an attachment material that is used to form an attachment that is to be attached to the exterior surface of the tooth and having a first opening to allow the attachment material to be placed in contact with the exterior surface of the tooth; and a release liner formed over the first opening to retain the attachment material within the well portion. The well portion of the first surface may include a second opening that allows for the attachment material to be placed within the well while the release liner is positioned over the first opening. The well portion of the first surface may include a second opening that allows for air to exit the well when the attachment material is placed within the well. The appliance may further include an attachment positioned in the well and a light curable adhesive material on a surface of the attachment for attaching the attachment to the tooth. The light curable adhesive material may be in contact with the release liner. The appliance may include at least a second surface shaped to conform to the contours of an exterior surface of a second tooth. The appliance may include a portion of the second surface shaped to accommodate an attachment that is to be attached to the exterior surface of the second tooth.

According to a further embodiment, a dental attachment formation apparatus comprises: a body having a first surface shaped to conform to the contours of an exterior surface of a tooth and including a portion of the first surface shaped to accommodate an attachment that is to be attached to the exterior surface of the tooth; an attachment material that is used to form the attachment positioned within the well; and a first release liner formed over or under the attachment material to allow for the release of the attachment material within the well portion. The portion of the first surface may be shaped to accommodate an attachment that is to be attached to the exterior surface of the tooth is a well for the placement of a light curable material therein that is used to form the attachment. The first release liner may be formed under the attachment material and a second release liner is formed over the attachment material. At least a portion of the body may be made of an ultraviolet (UV) light transmissive material to allow UV light from the light source to cure a UV light curable material in contact with at least one of the first and second tooth. At least a portion of the body may be made of a light transmissive material to allow light from the light source to cure a light curable material in contact with the first tooth and wherein the material is configured to manipulate the light using one or more optical properties.

According to another embodiment, a dental appliance comprises: a body having a first surface shaped to abut an exterior surface of a tooth; and a well portion of the first surface shaped to form a well to accommodate an attachment material that is used to form an attachment that is to be attached to the exterior surface of the tooth and having a first opening to allow the attachment material to be placed in contact with the exterior surface of the tooth and having a second opening that allows for air to exit the well when the attachment material is placed within the well.

According to a further embodiment, an attachment formation structure system comprises: a body including a conformal surface shaped and configured to conform to contours of a buccal exterior surface of a tooth, the body including a well portion having a shape and orientation for forming an orthodontic attachment at a specified location on the buccal exterior surface of the tooth; attachment material positioned within the well portion and configured to form the orthodontic attachment on the tooth; and a release liner covering the well portion to retain the attachment material within the well portion. The attachment material may be directly fabricated within the well portion. The well portion may allow the attachment material to be placed in contact with the buccal exterior surface of the tooth when the body is positioned on a patient's teeth. The body may further include a light curable adhesive material on a surface of the attachment material for attaching the orthodontic attachment to the tooth. The light curable adhesive material may be an attachment composite material. At least a portion of the body may be made of a light transmissive material to allow light from a light source to cure a light curable material in contact with the tooth. At least a portion of the body may be made of a transparent material that is transparent to visible light. The body may be constructed of a flexible material that is configured to bend against the buccal exterior surface of the tooth. The attachment material may be sufficiently rigid to maintain a specified shape within the well portion. The attachment material may be directly fabricated with one or both of the body and the release liner. The body may include multiple segments that are separatable by one or more score lines, wherein the one or more score lines is configured to allow removal of at least a first segment of the multiple segments from one or more teeth while a second segment of the multiple segments remains on the one or more teeth.

According to another embodiment, an attachment formation structure system utilized in conjunction with a dental appliance to apply forces to reposition one or more teeth comprises: a body including a conformal surface shaped to conform to contours of an exterior surface of a tooth, the body including a well portion having an attachment material therein, wherein the well portion has a shape and orientation for forming an orthodontic attachment using the attachment material at a specified location, wherein an outer surface of the attachment material includes a layer of adhesive material that is configured to bond the orthodontic attachment to the exterior surface of the tooth; and a release liner covering the well portion to retain the layer of adhesive material and the attachment material within the well portion. The attachment material may be directly fabricated within the well portion and be configured to form the orthodontic attachment on the exterior surface of the tooth. The layer of adhesive material may be made of a light curable adhesive material. The light curable adhesive material may be in contact with the release liner. The conformal surface may be shaped to conform to contours of an exterior surface of a second tooth. The body may include a second well portion shaped to accommodate a second attachment material configured to form a second orthodontic attachment on the exterior surface of the second tooth.

According to a further embodiment, an attachment formation apparatus utilized in conjunction with a dental positioning appliance to apply forces to reposition one or more teeth comprises: a body including a conformal surface shaped and configured to conform to contours of a buccal exterior surface of a tooth, the body including a well portion having a shape and an orientation for forming an orthodontic attachment at a specified location on the buccal exterior surface of the tooth; an attachment material positioned within the well portion and configured to form the orthodontic attachment on the tooth, wherein an outer surface of the attachment material includes a layer of adhesive material that is configured to bond the orthodontic attachment to the buccal exterior surface of the tooth; and a release liner covering the well portion to retain the layer of adhesive material and the attachment material within the well portion, wherein the release liner conforms to a shape of the buccal exterior surface of the tooth. The attachment material may be directly fabricated within the well portion. The body may further include a light curable adhesive material on a surface of the attachment material for attaching the attachment material to the tooth. At least a portion of the body may be made of an ultraviolet (UV) light transmissive material to allow UV light from a light source to cure a UV light curable material in contact with the buccal exterior surface of the tooth. At least a portion of the body may be made of a light transmissive material to allow light from a light source to cure a light curable material in contact with the tooth and wherein the light transmissive material is configured to manipulate the light using one or more optical properties.

According to another embodiment, an attachment formation structure system utilized in conjunction with a dental positioning appliance to apply forces to reposition one or more teeth comprises: a body including: a conformal surface shaped and configured to be positioned against and conform to contours of a buccal exterior surface of a tooth; a well portion having an attachment material therein and a shape and an orientation for forming an orthodontic attachment from the attachment material at a specified location on the buccal exterior surface of the tooth; and a release liner covering the well portion to retain the attachment material within the well portion; wherein the body includes a first segment coupled to a second segment at a score line therebetween, wherein the score line is configured to allow removal of the first segment from the one or more teeth while the second segment remains on the one or more teeth. The attachment material may be directly fabricated within the well portion and be configured to form the orthodontic attachment on the buccal exterior surface of the tooth. The body may be constructed of a flexible material that is configured to bend against the buccal exterior surface of the tooth.

DETAILED DESCRIPTION

The present disclosure provides methods, computing device readable medium, devices, and systems having a dental attachment formation structure. Such solutions should make forming, positioning, orienting and securing attachments easier and quicker, and can make the patient's experience better than use of past procedures.

One dental appliance includes a body having a first surface shaped to abut an exterior surface of a tooth and a well portion of the first surface shaped to form an attachment that is to be attached to the exterior surface of the tooth, a release layer formed over a surface of the well to allow the attachment to be removed from the well, and an attachment material that is used to form the attachment positioned within the well. Such an embodiment, as will be discussed below with regard to the figures, can provide better uniformity to the desired shape of the attachment and/or can provide better positioning of the attachments on the surface of the patient's tooth, among other benefits.

In the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

As used herein, the designators "M" and "N", particularly with respect to reference numerals in the drawings, indicate that any number of the particular feature so designated can be included. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 328 may reference element "28" in FIG. 3, and a similar element may be referenced as 428 in FIG. 4.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

Figure 1A:
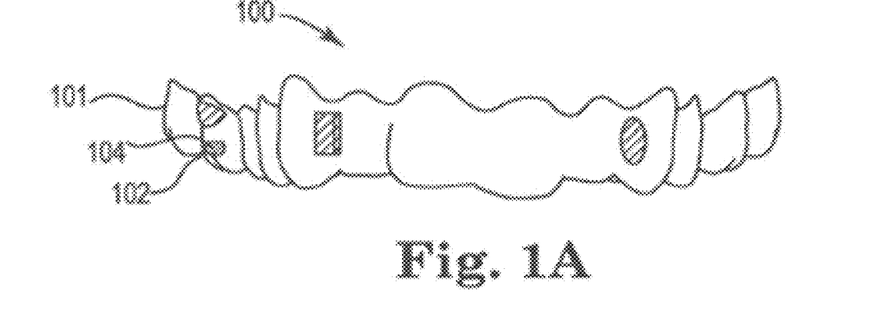
FIG. 1A illustrates a front view of a dental attachment formation appliance according to a number of embodiments of the present disclosure.
Figure 1B:
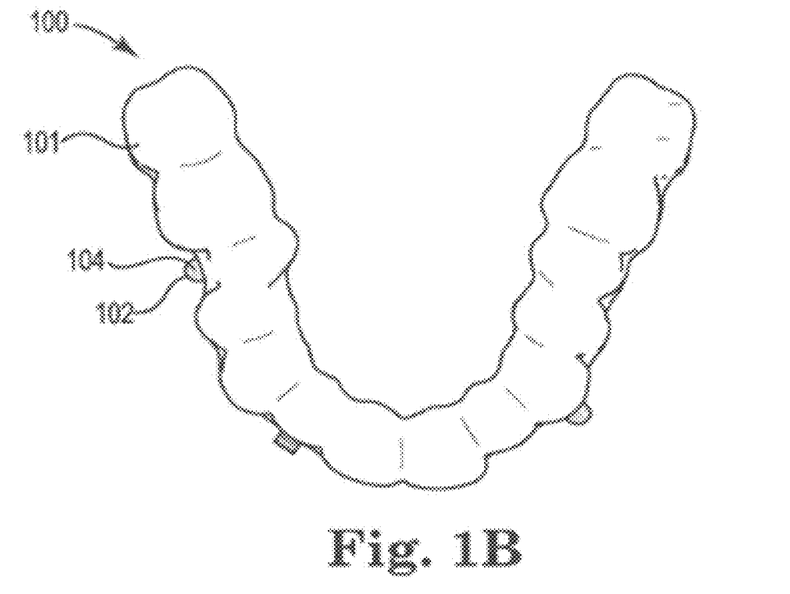
FIG. 1B illustrates a top view of a dental attachment formation appliance according to a number of embodiments of the present disclosure.

FIG. 1A illustrates a front view of a dental attachment formation appliance according to a number of embodiments of the present disclosure. FIG. 1B illustrates a top view of a dental attachment formation appliance according to a number of embodiments of the present disclosure. In the embodiment of FIGS. 1A and 1B, the apparatus 100 (an appliance) includes a body 101 having a surface shaped to conform to the contours of at least one exterior surface of a tooth (in this example embodiment, the body has surfaces to conform to the buccal, lingual, and occlusal surfaces of the teeth). The body 101 also includes a number of wells 102 formed in the appliance to provide a template for the shape of the attachments and position and orientation of the attachments on one or more teeth of the patient. These wells are then filled with attachment formation material 104 that will be cured to form the attachment.

This can be beneficial for a number of reasons. For example, the uncured material can be placed in the well, then the entire structure can be pressed against the surface of the tooth. This process compresses the material and forces it to conform to the surfaces (of the well and of the tooth). This can provide a better mating engagement between the surface of the tooth and a surface of the attachment that will be used to secure the attachment to the tooth.

In some embodiments, one or more portions or all of the apparatus can be made from a light transmissive material to allow light from the light source to cure a light curable material in contact with the tooth. The light transmissive material can be transmissive to visible light or certain wavelengths of light such as ultraviolet (UV) wavelengths or any other desirable wavelength range.

In prior concepts, treatment professionals may only have had access to a few standardized attachment shapes. In this manner, the options for treatment may have been restricted based on the limited forces that could be provided by the standardized attachment shapes. If any other attachment shape was desired, the treatment professional could file or grind the attachment surfaces to change its shape. This resulted in additional time spent in getting the proper shape, misshapen attachments that did not fit or function correctly, and other issues.

Although embodiments of the present disclosure can be used to form such standardized attachment shapes, in some embodiments of the present disclosure, specialized attachments can be made available to a treatment professional, wherein the specialized attachments are formed using the templates provided to the treatment professional. These templates can be designed based on the forces specifically needed during treatment with regard to each specific patient. The templates can provide for precise positioning, orientation, and/or attachment and, in some embodiments, include premixed attachment material, which can provide precise selection of the type of attachment material, of the mixture material, and/or placement of the attachment material in the well.

Such specialization can also, for example, include the size of the attachment, shape of the attachment, and other suitable specialized characteristics. Examples, of various sized and shaped attachments are shown in FIGS. 1A and 1B. Accordingly, the patient will get a more customized treatment based on use of such embodiments. This can allow the attachment to be specialized to the patient, but not be onerous on the treatment professional who, for example, may not have attachment design skills or capabilities.

In some embodiments, the treatment professional may also select one or more attachment materials or attachment types and/or select the location upon which they should be applied. Such embodiments can allow further customization of the attachment and can be taken into account when the manufacture of the attachment templates are created. Further, in various embodiments, this customization can be made for each appliance (or for multiple appliances) in a set of appliances of a treatment plan.

For example, through use of the treatment plan and/or virtual modeling, a dental appliance (e.g., an aligner for aligning teeth or jaws of a patient) can be made, for example, by thermal-forming a sheet of plastic over a physical dental mold. The physical dental mold, for instance, can represent an incremental position to which a patient's teeth are to be moved and can include attachment shapes formed in the mold.

In this manner, one or more surfaces of the dental appliance can engage with one or more surfaces of the one or more attachments (when the finished dental appliance is placed in the patient's mouth with the actual attachments). By having the attachments on the mold, the dental appliance is formed with the surfaces that will interact with the attachments.

The physical dental mold can be manufactured, for example, by downloading a computer-aided design (CAD) virtual dental model to a rapid prototyping process, such as, for example, a computer-aided manufacturing (CAM) milling, stereolithography, and/or photolithography process.

The dental mold (e.g., set of molded teeth and/or jaw) can be created from a virtual model of a number of teeth and/or jaw of a patient. A virtual model, for example, can include an initial virtual dental model and/or intermediate virtual dental model (wherein the teeth of the patient have been moved with respect to their actual physical position). A dental mold can be formed in accordance with a unique treatment file that, for example, identifies a patient, a stage of a treatment plan, the virtual model of the number of teeth and/or jaw, and/or whether the dental mold is of the upper and/or lower dental arch.

In some computing device system processes, a treatment file can be accessed by a rapid prototyping machine or direct fabrication device, such as a SLA or 3D printing machine, to form and/or create the dental mold. As discussed above, the result of the dental mold can include a set of molded teeth.

The set of molded teeth can include at least a replica of a number of teeth of the patient, but can also include features such as gingival and jaw structures, among others. The dental mold can be used to make a dental appliance, for example, by creating a negative impression of the dental mold using polymeric sheets of material and vacuum forming the sheets over the dental mold, as discussed above. Generally, the dental appliance is produced and/or formed by heating a polymeric thermoformable sheet and vacuum or pressure forming the sheet over the dental mold (e.g., a number of molded teeth). A dental appliance can, for example, include a negative impression of the dental mold.

Such molding techniques can be used to create the templates for forming the attachments. In some embodiments, a mold used to create the dental appliance can be used to form an attachment template. However, in some embodiments, the template may be a generally planar sheet of material with a well formed therein that can be applied to an exterior surface of the tooth. This may be useful in instances where the treatment professional is skilled at positioning and/or orienting the attachment on the surface of a tooth.

In instances where the treatment professional is not as proficient in positioning and/or orienting the attachment, the template may include one or more engagement surfaces that can engage a surface of the patient's tooth to aid in proper positioning and/or orientation. As used herein, "positioning" is the locating of the attachment at a particular point on the surface of a tooth and "orienting" is the movement of the attachment in a manner that does not change its position on the surface of the tooth (e.g., a rotation of the attachment about an axis or movement of the attachment in one or more directions that does not change its position on the surface of the tooth). For example, an attachment can be positioned at a particular point on the surface of a tooth and then can be oriented by rotating it, for example, parallel to the tooth surface, or along an axis perpendicular to the surface of the tooth. Other angles of rotation can also be used to orient the attachment without changing the attachment's position.

Figure 2:
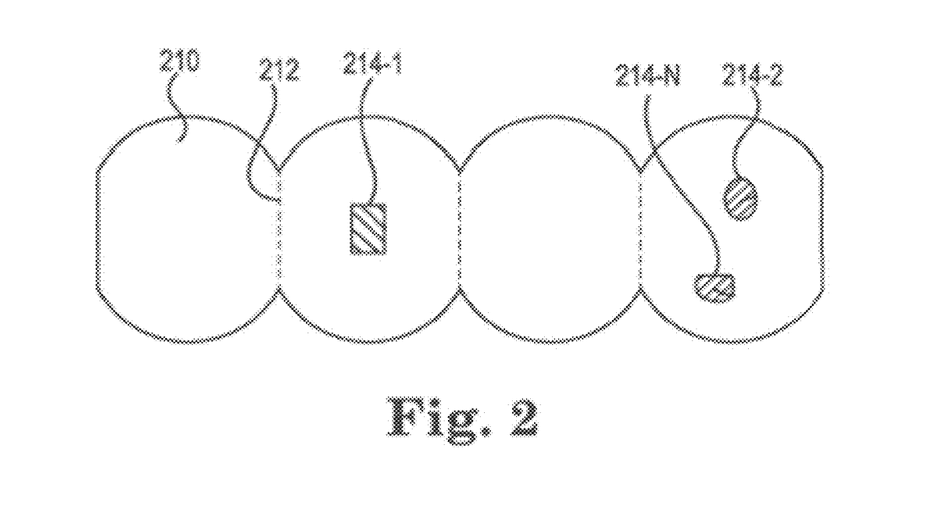
FIG. 2 illustrates a front view of an attachment formation appliance according to a number of embodiments of the present disclosure.

FIG. 2 illustrates a front view of an attachment formation appliance according to a number of embodiments of the present disclosure. In the embodiment of FIG. 2, the apparatus (i.e., template) includes a body 210 having multiple wells 214-1, 214-2, and 214-N formed on one surface that is to be applied to a tooth. In this embodiment, the right most section has two wells formed therein. Additionally, the section second from the left includes one well formed therein. As can be seen from such embodiments, multiple wells can be formed on the same section and/or on multiple sections of the apparatus.

In some embodiments, the template may not be tooth shaped (e.g., may not have an elongate surface that is shaped similar to the exterior surface of a tooth). As shown, the template may be any suitable shape that will allow the attachment material to contact the surface of the tooth for purpose of securing the attachment to the tooth.

For example, in some embodiments, the template may be relatively planar with the exception of the wells. This may be beneficial, for example, because the cost and time in manufacturing a planar template may be less than a tooth contoured template.

Further, in various embodiments, the template may be constructed of flexible material, allowing the material to be bent against the exterior surface of the tooth. As discussed above, this may reduce cost and/or time in manufacturing, among other benefits.

The template may also be constructed of material that can be segmented or cut such that each section can, for example, be applied to non-adjacent teeth. One benefit of creating multiple attachments for different, non-adjacent teeth on adjacent sections is that cost and time in manufacturing may be reduced. For example, in FIG. 2, score lines 212 can be positioned to allow portions of the template to be selectively removed such that one segment or more than one segment can be separated from the other segments (e.g., left most segment can be separated from the other three segments).

Additionally, in some embodiments (like the right most section of the template body) multiple attachments can be created on one section and applied on different teeth. For example, the oval shaped attachment 214-2 could be secured to a first tooth and the oval shaped attachment 214-2 could be secured to the first tooth (e.g., by selectively curing the oval attachment 214-2 and not the non-oval shaped attachment 214-N). The section could then be moved from the first tooth (leaving the oval attachment 214-2 secured to that tooth) to a second tooth, where the non-oval 214-N shaped attachment can be secured to the second tooth (e.g., by curing the non-oval shaped attachment 214-N). As discussed above, in such an embodiment, one attachment could be placed and cured on a first tooth and the second attachment could subsequently be placed and cured on a second tooth once the first attachment has been removed from the template (attached to the first tooth).

In some embodiments, the body includes several registration surfaces that, when properly aligned against a particular surface of a tooth, can be used to aid in positioning and/or orientation of the attachment with respect to an exterior surface of the tooth. For example, registration surfaces can be used to engage: the front surface of the tooth, the bottom edge of the tooth, a first side edge of the tooth, and/or similar surfaces on the one or more other teeth that will engage surfaces on the template that may not have attachments on them. As such, one or more such surfaces can be used to aid in the correct positioning and/or orientation of the template and thereby the attachment, which can be beneficial, in some implementations.

In some such embodiments, different light sources can be provided directed to the template to allow one attachment to be cured while the one or more other attachments are not cured until they are positioned on their respective tooth. For example, the left, middle, and/or right sections can have different light sources or have the light source directed to the attachment thereon at different times allowing them to cure the material in their wells at different times or at substantially the same time.

Such embodiments would also allow the sections to be separated for placement and curing. For example, with respect to the embodiment of FIG. 2, the four sections can be separated from each other or two sections can be removed and the other two kept together.

Some embodiments may have portions that are opaque to the light used to cure the attachments, such that the opaque portions keep the light from curing material until it is intended to be cured. For example, a template may have three attachment wells and a light source may only illuminate a specific one of the attachment wells when a light is directed toward that corresponding attachment.

Some such embodiments may allow light to illuminate multiple wells. For example, if two attachments are to be attached to one tooth and a third attachment to a second tooth, the two attachments may be illuminated at the same time to cure them in their particular positions and orientations relative to each other and/or the tooth surface and the third may be separated by an opaque material, such that it can be applied to a second tooth at a later time.

Figure 3A:
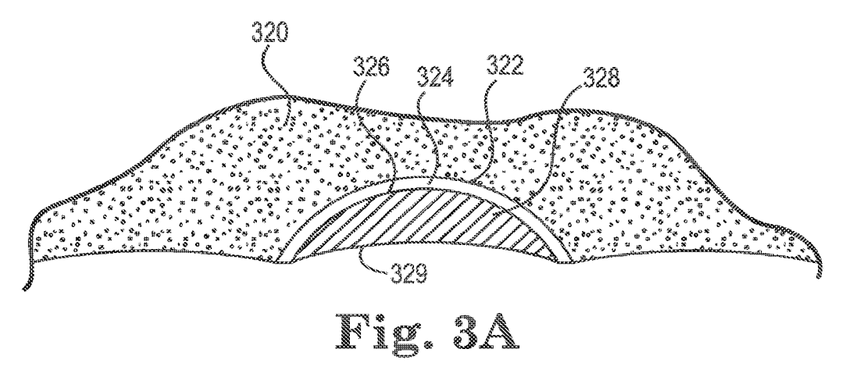
FIG. 3A illustrates a cutaway view of an attachment formed in an appliance according to a number of embodiments of the present disclosure.

FIG. 3A illustrates a cutaway view of an attachment formed in an appliance according to a number of embodiments of the present disclosure. The embodiment of FIG. 3A includes a dental attachment formation appliance body 320 with a well surface 322 forming a well for placement of material to form an attachment.

In some embodiments, as shown in FIG. 3A, the well can have a release material 324 provided therein. On an outer surface of the release material 326, the attachment material 328 can be applied. The outer surface of the attachment material 329 can include an adhesive material to allow the attachment to be adhered to the surface of a tooth. In some embodiments, a release material (e.g., a material applied over the attachment material or an item such as a releasable liner can be used, for example) can be positioned over the attachment material or adhesive material, if used.

As discussed above, in some embodiments, at least a portion of the body can be made of a light transmissive material (e.g., transmissive to UV, visible light, etc.) to allow light from the light source to cure a light curable material in contact with at least one of the first and second tooth. In order to cure the curable material, the light directed from the light source (or light path) has to be close enough to provide enough light to cure the material. However, embodiments that have a portion that is transmissive can allow the end of the light path or light source to be located further away from the well, allowing for more design options with regard to the positioning and orientation of the one or more light sources/light paths and the one or more wells.

In another embodiment, the dental attachment formation apparatus includes a body having a surface shaped to conform to the contours of an exterior surface of a tooth (as shown in FIGS. 1A and 1B). The surface includes a portion of the surface shaped to accommodate an attachment that is to be attached to the exterior surface of the tooth.

Figure 3B:
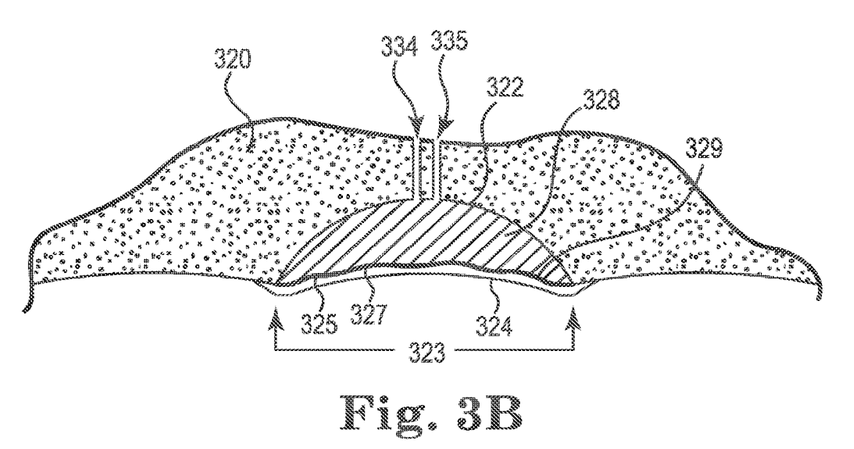
FIG. 3B illustrates a cutaway view of another attachment formed in an appliance according to a number of embodiments of the present disclosure.

FIG. 3B illustrates a cutaway view of another attachment formed in an appliance according to a number of embodiments of the present disclosure. The embodiment of FIG. 3B includes a dental attachment formation appliance body 320 with a well.

In the embodiment illustrated in FIG. 3B, the well is filled with the attachment formation material (i.e., curable material or other suitable material for forming an attachment) 328 without a release liner between the well surface 322 and the attachment formation material 328. However, some embodiments can include a release material between the well surface and the attachment formation material.

The embodiment of FIG. 3B also includes multiple openings in the appliance that can provide a number of functions. For example, an opening 323 can be utilized to allow the attachment formation material 328 to contact the exterior surface of a tooth in preparation for attaching the attachment, for example, with adhesive 327 or via curing the attachment formation material 328 directly to the tooth, as can be done in some implementations.

In some embodiments opening 323 can be used to deposit the attachment formation material (and/or releasable material) into the well. In addition to or alternatively to the use of opening 323 to deposit material, openings 334 and/or 335 can be utilized to deposit the attachment formation material (and/or releasable material) into the well.

In some embodiments one or both openings 334 and/or 335 can be used as a vent to allow air to exit the well when the attachment formation material is placed within the well. In one embodiment, a release liner 324 is provided over opening 323, attachment formation material is deposited into the well through opening 334, and opening 335 is used as a vent to ensure that most or all of the air leaves the interior of the well and is replaced by attachment formation material.

The adhesive material that can be used to attach an attachment to a tooth surface can be any suitable adhesive and can, for example be a form of composite material such as: a micro, nano, hybrid, and/or flowable composite material. As with the releasable materials, the adhesive materials can be applied in any suitable manner, such as by spraying, painting, or via a layer of adhesive material.

As can be seen by the embodiment of FIG. 3B, the surface of the attachment 329 that is to be attached to the exterior surface of the tooth can have a specially contoured surface formed to create a best attachment surface with respect to the tooth. Such surfaces can include a surface that will mate with the exterior surface of the tooth or a surface having texture (random or designed structures, like an abrasive or patterned surface) thereon that may increase the ability of the adhesive of curing material to attach to the surface of the tooth.

In some embodiments, the attachment material and/or the adhesive material can be malleable, such that the surface can be changed before or during positioning on the surface of the tooth. For example, in some embodiments, the appliance can have a releasable material over the attachment material and/or the adhesive material and when the releasable material is removed and the attachment material and/or the adhesive material is placed in contact with the surface of the tooth, the surface of the attachment material and/or the adhesive material conforms to a mating shape with the tooth surface.

In some embodiments, the releasable material 324 can be rigid enough to shape the surface of the attachment material 329 and/or the adhesive material 325 when the releasable material is placed over the opening 323. In this manner, the shape of the attachment can be customized to each individual patient and, more specifically, each individual tooth. Further, in some embodiments, the attachment material and/or the adhesive material can be sufficiently rigid to maintain a specific shape and the releasable material can be flexible to conform to the specific shape of the surface of the attachment material and/or the adhesive material.

Figure 4:
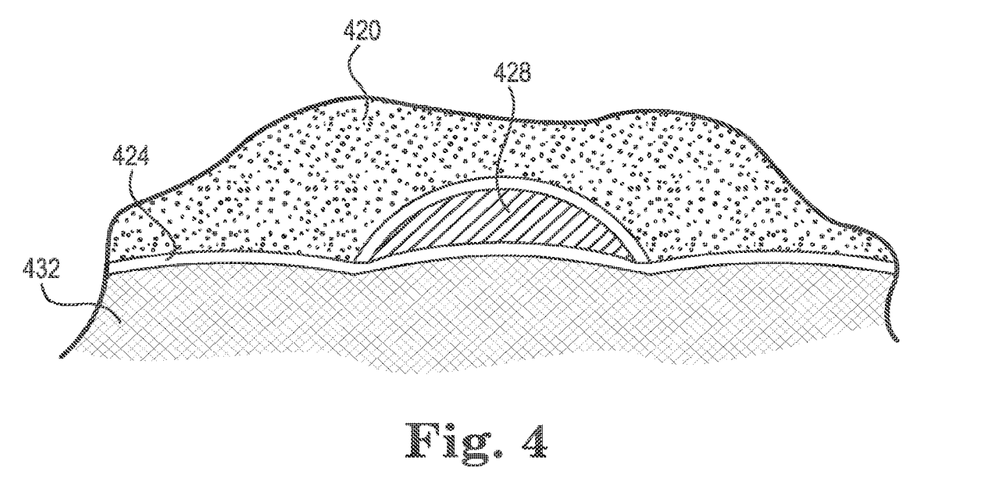
FIG. 4 illustrates a cutaway view of another attachment formed in an appliance according to a number of embodiments of the present disclosure.

FIG. 4 illustrates a cutaway view of another attachment formed in an appliance according to a number of embodiments of the present disclosure. In the embodiment of FIG. 4, an attachment is formed on a model of a tooth surface 432. In this embodiment, a release material is positioned between the surface of the well and the attachment material 428, such that the attachment material can be removed from the well. The embodiment also includes a release liner 424 to allow the template and/or the attachment to be removed from the surface of the model 432. In some embodiments, this release liner can be removed from the surface of the model 432 with the body 420 and attachment material 428 to retain the attachment material within the well until it is ready to be placed on the tooth of a patient at which point the release liner (or other type of releasable material) can be removed and the attachment material placed in contact (directly or indirectly, via an adhesive layer) with the surface of the tooth.

As discussed above, the template can be a body that is placed in contact with the exterior surface of the tooth in a manner such that the attachment will be either in direct contact or in indirect contact (i.e., in contact via the adhesive) in order to facilitate bonding of the attachment to the surface of the tooth. Further, as discussed above, the attachment material and/or adhesive material can be positioned in the well by a treatment professional, some time during the manufacturing of the template, or after the manufacturing is complete.

One benefit of having a manufacturer fill the well is that it can be done with more precision and/or consistency than if different treatment professionals are filling the wells when they arrive. One benefit of having the treatment professional fill (at least partially) the well is that they may be able to put the appropriate amount of material in the well to create the best adhesion to the exterior surface of the tooth.

Figure 5:
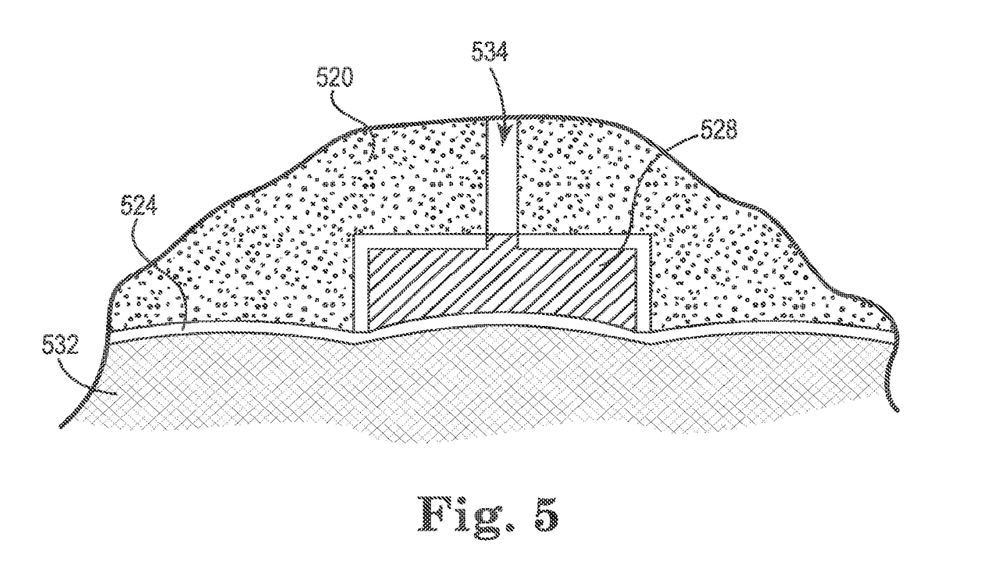
FIG. 5 illustrates a cutaway view of another attachment formed in an appliance according to a number of embodiments of the present disclosure.

FIG. 5 illustrates a cutaway view of another attachment formed in an appliance according to a number of embodiments of the present disclosure. In the embodiment of FIG. 5, an attachment is formed on a model of a tooth surface 532. In this embodiment, a release material is positioned between the surface of the well and the attachment material 528, such that the attachment material can be removed from the well. The embodiment also includes a release material 524 to allow the template and/or the attachment to be removed from the surface of the model 532. As with the embodiment of FIG. 4, the embodiment of FIG. 5 allows for this release material or a portion of the material to be removed from the surface of the model 532 with the body 520 and attachment material 528 to retain the attachment material within the well until it is ready to be placed on the tooth of a patient at which point the release liner (or other type of releasable material) can be removed and the attachment material placed in contact (directly or indirectly, via an adhesive layer) with the surface of the tooth.

FIG. 5 also includes a first opening. This first opening is the wide opening to the well, in the embodiment of FIG. 5, that is covered by the release material 524 and is used, for example, to allow the attachment material to be placed onto the surface of the tooth and, for example, allows the attachment, once secured to the tooth, to be removed from the template.

FIG. 5 also includes a second opening. The second opening 534 can, for example, be used to insert one or more of attachment material, releasable material, and/or adhesive material into the well. This can be beneficial, for instance, when a release liner 524 or model 532 is already positioned over the first opening of the well. Second opening 534 can also be used as a vent to allow ambient air to be removed from the well as one or more of the above materials are added into the well.

Figure 6:
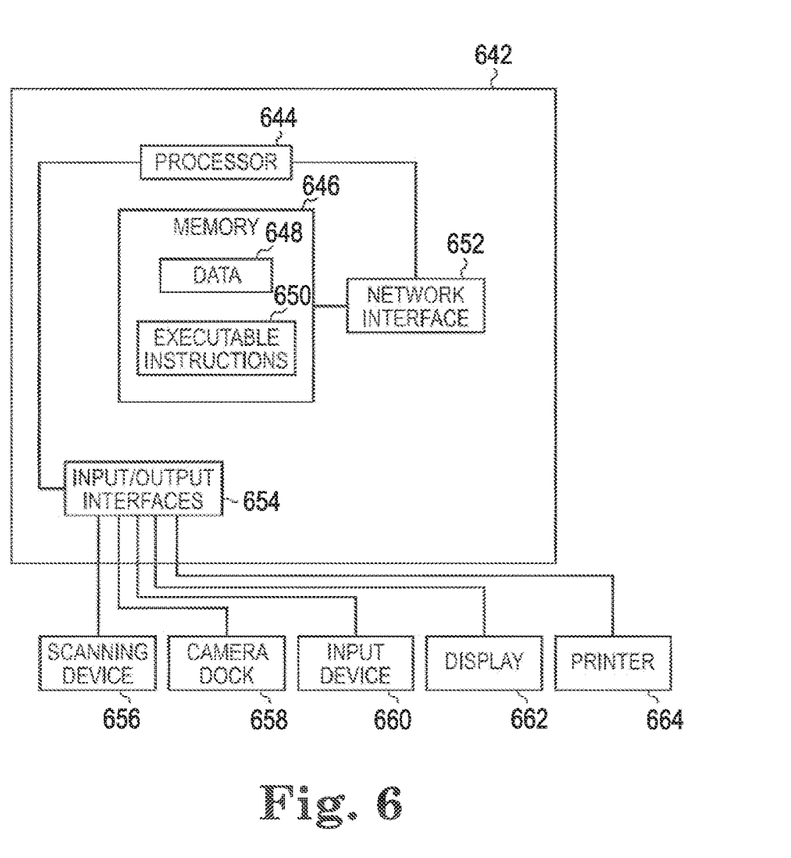
FIG. 6 illustrates a computing device that can be utilized according to one or more embodiments of the present disclosure.

FIG. 6 illustrates a computing device that can be utilized according to one or more embodiments of the present disclosure. For instance, a computing device 642 can have a number of components coupled thereto.

The computing device 642 can include a processor 644 and a memory 646. The memory 646 can have various types of information including data 648 and executable instructions 650, as discussed herein.

The processor 644 can execute instructions 650 that are stored on an internal or external non-transitory computer device readable medium (CRM). A non-transitory CRM, as used herein, can include volatile and/or non-volatile memory.

Volatile memory can include memory that depends upon power to store information, such as various types of dynamic random access memory (DRAM), among others. Non-volatile memory can include memory that does not depend upon power to store information.

Memory 646 and/or the processor 644 may be located on the computing device 642 or off of the computing device 642, in some embodiments. As such, as illustrated in the embodiment of FIG. 6, the computing device 642 can include a network interface 652. Such an interface 652 can allow for processing on another networked computing device, can be used to obtain information about the patient, and/or can be used to obtain data and/or executable instructions for use with various embodiments provided herein.

As illustrated in the embodiment of FIG. 6, the computing device 642 can include one or more input and/or output interfaces 654. Such interfaces 654 can be used to connect the computing device 642 with one or more input and/or output devices 656, 658, 660, 662, 664.

For example, in the embodiment illustrated in FIG. 6, the input and/or output devices can include a scanning device 656, a camera dock 658, an input device 660 (e.g., a mouse, a keyboard, etc.), a display device 662 (e.g., a monitor), a printer 664, and/or one or more other input devices. The input/output interfaces 654 can receive executable instructions and/or data, storable in the data storage device (e.g., memory), representing a virtual dental model of a patient's dentition.

In some embodiments, the scanning device 656 can be configured to scan one or more physical dental molds of a patient's dentition. In one or more embodiments, the scanning device 656 can be configured to scan the patient's dentition and/or a dental appliance directly. The scanning device 656 can be configured to input data into the computing device 642.

In some embodiments, the camera dock 658 can receive an input from an imaging device (e.g., a 2D or 3D imaging device) such as a digital camera, a printed photograph scanner, and/or other suitable imaging device. The input from the imaging device can, for example, be stored in memory 646.

The processor 644 can execute instructions to provide a visual indication of a treatment plan, a dental appliance, and/or a one or more attachments on the display 662. The computing device 642 can be configured to allow a treatment professional or other user to input treatment goals. Input received can be sent to the processor 644 as data 648 and/or can be stored in memory 646.

Such connectivity can allow for the input and/or output of data and/or instructions among other types of information. Some embodiments may be distributed among various computing devices within one or more networks, and such systems as illustrated in FIG. 6 can be beneficial in allowing for the capture, calculation, and/or analysis of information discussed herein.

The processor 644, in association with the data storage device (e.g., memory 646), can be associated with the data 648. The processor 644, in association with the memory 646, can store and/or utilize data 648 and/or execute instructions 650 for creating and/or modeling interactions between an attachment and a tooth; interactions between an attachment and an appliance; and/or combinations of interactions between one or more attachments, one or more teeth and/or other structure in the mouth of the patient, and/or one or more appliances for moving teeth. The processor 644, in association with the memory 646 can, in addition to or alternatively, store and/or utilize data 648 and/or execute instructions 650 for creating and/or modeling attachment structures, attachment wells, attachment templates, and/or adhesive and/or releasable materials, as well as a virtual modeling of such items with or without a template appliance, appliance for moving teeth, and/or one or more teeth.

The virtual model of the dental appliance and/or attachments to attach a dental appliance to the teeth of a patient can be used to create a physical dental appliance and/or attachments, for instance, as discussed further herein. Such a virtual model or similar modeling technique can also be used to form a template (e.g., an appliance to form one or more attachments).

The processor 644 coupled to the memory 646 can, for example, include instructions to cause the computing device 642 to perform a method including, for example, providing a virtual model of a dental appliance having a shell configured to reposition a number of teeth of a patient or a template appliance for the formation of one or more attachments. In some embodiments, instructions can be provided to fill one or more wells with attachment material, shape the material within the one or more wells, and/or apply one or more releasable materials to one or more wells, through direction of a direct fabrication device or other such device.

In some embodiments, the processor 644 coupled to the memory 646 can cause the computing device 642 to perform the method comprising providing a treatment plan for the patient. The treatment plan can include a virtual model of a dental appliance having a shell configured to reposition at least one tooth of the patient. The virtual model can also include identification of a placement position and/or orientation of one or more attachments.

In various embodiments, the processor 644 coupled to the memory 646 can cause the computing device 642 to perform the method comprising virtually testing the attachment shape, location, orientation, type of attachment material to be used, and other suitable attachment characteristics to determine the best attachment and/or placement of the attachment.

Such analysis can be accomplished one or more times for a treatment plan. For example, if a treatment plan has 30 stages, it would be possible to have different attachments for each stage or possibly more, if desired. However, in many instances the attachment type, position, and/or orientation may be changed a few times during the treatment plan.

Through use of virtual modeling, attachments can be virtually tested and the best attachment type, shape, position, and/or orientation can be selected without inconveniencing the patient with trial and error of attachments during treatment. Additionally, use of virtual modeling can also allow for custom design of attachment shapes that will be suitable for a specific patient's needs and/or a specific function within an area of a patient's mouth.

Further, the specialized nature of the design of such attachments can also allow the attachments to be made from different materials. In this manner, attachments during a treatment plan or even during one stage can be of a different material that may provide more specialized force distribution than was possible with standard attachments.

In some embodiments, the printer 664 can be a three dimensional or direct fabrication device that can create a dental appliance directly from instructions from the computing device 642. Embodiments of the present disclosure utilizing such technology can be particularly beneficial for a variety of reasons. For example, such direct manufacture allows for less waste of materials due to less processing steps and increased specialization of the template, wells, attachment materials, and/or other components of the appliances described herein.

In some embodiments, the template can be formed and one or more wells filled with attachment formation material. Such technologies can be particularly useful in some such embodiments as the surface of the attachment material and/or the adhesive material that will contact the tooth can be formed in a specialized shape as directed by the computing device. Further, in some embodiments, the shape of the releasable material can be specialized (as discussed with respect to FIG. 3B).

Additionally, virtual modeling can be beneficial, for example, because the volume of a well can be calculated and the amount of material and/or type of material used to fill the well can be accurately calculated, thereby reducing waste and leaving less potential for error by the treatment professional. This can be further improved in some implementations when the attachment material is placed in the well prior to delivery to the treatment professional or when a computing device directs the manufacture of the attachment and/or template via direct fabrication.

The embodiments of the present disclosure can provide a number of benefits. For example, the embodiments can save time and cost in manufacture, improve the accuracy of the type of attachment material used, the preparation of the material, formation of the attachments, the positioning and/or orientation of the placement of the attachments, allow more ability to create specialized attachment sizes and shapes, and can save time and improve the experience of the patient and/or treatment professional in creating and/or securing attachments, among other benefits.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of bonding an orthodontic attachment to a tooth of a patient, the method comprising:
  receiving an attachment placement structure, the attachment placement structure including a well holding the orthodontic attachment therein, the orthodontic attachment having a mating surface at a first opening of the well, wherein the mating surface of the orthodontic attachment is shaped to conform to a contour of a buccal surface of the tooth, wherein the attachment placement structure further includes:
    one or more registration surfaces that conform to one or more occlusal surfaces of the patient's teeth to aid in proper positioning or orientation of the orthodontic attachment;
    a release liner covering the first opening of the well and covering the mating surface of the orthodontic attachment; and
    one or more second openings that provide sole access to the well holding the orthodontic attachment;
  removing the release liner from the mating surface of the orthodontic attachment;
  placing the attachment placement structure on the patient's dentition to position the orthodontic attachment at a specified location with respect to the buccal surface of the tooth; and
  bonding the mating surface of the orthodontic attachment to the buccal surface of the tooth.

2. The method of claim 1, further comprising rotating the orthodontic attachment from a first orientation to a second orientation after placement of the attachment placement structure.

3. The method of claim 1, wherein the attachment placement structure is made of flexible material configured to be able to bend against an exterior surface of the tooth.

4. The method of claim 1, wherein the attachment placement structure comprises multiple placement structures for different sections of the patient's dentition.

5. The method of claim 1, further comprising removing the attachment placement structure from the patient's dentition.

6. The method of claim 1, wherein the orthodontic attachment is directly bonded to the buccal surface of the tooth.

7. The method of claim 1, wherein the orthodontic attachment is bonded to the buccal surface of the tooth via an adhesive.

8. The method of claim 1, wherein bonding the orthodontic attachment to the buccal surface of the tooth comprises exposing a curable adhesive material to light.

9. The method of claim 1, wherein the one or more registration surfaces are further configured to conform to a lingual surface of the patient's teeth.

10. The method of claim 1, further comprising placing a dental appliance on the patient's dentition after the orthodontic attachment is bonded to the buccal surface of the tooth, wherein the dental appliance engages with the orthodontic attachment and applies controlled forces on the patient's teeth.

11. The method of claim 10, wherein the dental appliance is an aligner, wherein the aligner generally conforms to the patient's teeth but is slightly out of alignment with a current tooth configuration.

12. The method of claim 1, wherein the attachment placement structure is three-dimensionally fabricated.

13. An attachment positioning apparatus comprising:
  a well holding an orthodontic attachment therein, the orthodontic attachment having a mating surface at a first opening of the well, wherein the mating surface of the orthodontic attachment is shaped to conform to a contour of a buccal surface of a patient's tooth;
  one or more registration surfaces that are shaped to conform to one or more occlusal surfaces of the patient's teeth, wherein the one or more registration surfaces are configured to aid in proper positioning or orientation of the orthodontic attachment;

a release liner covering the first opening of well and covering the mating surface of the orthodontic attachment; and one or more second openings that provide sole access to the well holding the orthodontic attachment, wherein when the attachment positioning apparatus is placed on the patient's dentition, the orthodontic attachment is positioned at a specified location with respect to the buccal surface of the patient's tooth.

14. The attachment positioning apparatus of claim 13, wherein the attachment positioning apparatus is made of flexible material configured to be able to bend against an exterior surface of a tooth.

15. The attachment positioning apparatus of claim 13, wherein the attachment positioning apparatus comprises multiple structures for different sections of the patient's dentition.

16. The attachment positioning apparatus of claim 13, wherein the orthodontic attachment is configured to be directly bonded to the buccal surface of the patient's tooth.

17. The attachment positioning apparatus of claim 13, wherein the orthodontic attachment is configured to be bonded to the buccal surface of the patient's tooth via a light curable adhesive.

18. The attachment positioning apparatus of claim 13, wherein the attachment positioning apparatus further comprises one or more second registration surfaces that are configured to conform to a lingual surface of the patient's teeth.

19. The attachment positioning apparatus of claim 13, wherein the attachment positioning apparatus is three-dimensionally fabricated.

20. An attachment positioning apparatus comprising:

a plurality of wells holding a plurality of corresponding orthodontic attachments therein, wherein each of the plurality of orthodontic attachments has a mating surface at a first opening of a corresponding well, wherein the mating surface of each of the plurality of orthodontic attachments is shaped to conform to a contour of a buccal surface of a corresponding patient's tooth, wherein each of the plurality of wells comprises:

a release liner covering the first opening of well and covering the mating surface of the corresponding orthodontic attachment; and one or more second openings that provide sole access to the well holding the corresponding orthodontic attachment; and one or more registration surfaces that are shaped to conform to one or more occlusal surfaces of the patient's teeth, wherein the one or more registration surfaces are configured to aid in proper positioning or orientation of the plurality of orthodontic attachments;

wherein when the attachment positioning apparatus is placed on the patient's dentition, the plurality of orthodontic attachments are positioned at specified locations with respect to the buccal surfaces of corresponding teeth.

* * * * *